US006378386B1

United States Patent
Schroder et al.

(10) Patent No.: US 6,378,386 B1
(45) Date of Patent: Apr. 30, 2002

(54) SURFACE CLEANLINESS MEASUREMENT PROCEDURE

(75) Inventors: Mark Stewart Schroder, Hendersonville, NC (US); Donald Ernest Woodmansee, Simpsonville; Douglas Frank Beadie, Greenville, both of SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/888,535

(22) Filed: Jun. 26, 2001

Related U.S. Application Data

(62) Division of application No. 09/669,574, filed on Sep. 26, 2000.

(51) Int. Cl.$^7$ ................................................. G01N 1/00
(52) U.S. Cl. .................................................. 73/864.71
(58) Field of Search ............................ 73/864.71, 104, 73/865.5; 356/237.2, 237.3, 244, 864.71

(56) References Cited

U.S. PATENT DOCUMENTS

| | | | |
|---|---|---|---|
| 2,835,246 A | | 5/1958 | Boettger |
| 3,074,276 A | | 1/1963 | Moos |
| 3,091,967 A | | 6/1963 | Hurdlow |
| 3,572,128 A | * | 3/1971 | Hemeon ................... 73/864.71 |
| 4,103,553 A | * | 8/1978 | De Blasiis et al. ...... 73/864.71 |
| 5,373,748 A | * | 12/1994 | Lioy et al. ............... 73/864.71 |
| 5,859,375 A | | 1/1999 | Danylewych-May et al. |
| 6,021,681 A | | 2/2000 | Jezek |

OTHER PUBLICATIONS

"39$^{th}$ GE Turbine State–of–the–Art Technology Seminar", Tab 1,""F" Technology—the First Half–Million Operating Hours", H.E. Miller, Aug. 1996.

(List continued on next page.)

*Primary Examiner*—Robert Raevis
(74) *Attorney, Agent, or Firm*—Nixon & Vanderhye PC

(57) ABSTRACT

A procedure and tools for quantifying surface cleanliness are described. Cleanliness of a target surface is quantified by wiping a prescribed area of the surface with a flexible, bright white cloth swatch, preferably mounted on a special tool. The cloth picks up a substantial amount of any particulate surface contamination. The amount of contamination is determined by measuring the reflectivity loss of the cloth before and after wiping on the contaminated system and comparing that loss to a previous calibration with similar contamination. In the alternative, a visual comparison of the contaminated cloth to a contamination key provides an indication of the surface cleanliness.

14 Claims, 4 Drawing Sheets

OTHER PUBLICATIONS

"39th GE Turbine State–of–the–Art Technlogy Seminar", Tab 2, "GE Heavy–Duty Gas Turbine Performance Characteristics", F. J. Brooks, Aug. 1996.

"39th GE Turbine State–of–the–Art Technology Seminar", Tab 3, "9EC 50Hz 170–MW Class Gas Turbine", A. S. Arrao, Aug. 1996.

"39th GE Turbine State–of–the–Art Technology Seminar", Tab 4, "MWS6001FA—An Advanced–Technology 70–MW Class 50/60 Hz Gas Turbine", Ramachandran et al., Aug. 1996.

"39th GE Turbine State–of–the–Art Technology Seminar", Tab 5, "Turbomachinery Technology Advances at Nuovo Pignone", Benvenuti et al., Aug. 1996/.

"39th GE Turbine State–of–the–Art Technology Seminar", Tab 6, "GE Aeroderivative Gas Turbines—Design and Operating Features", M.W. Horner, Aug. 1996.

"39th GE Turbine State–of–the–Art Technology Seminar", Tab 7, "Advance Gas Turbine Materials and Coatings", P.W. Schilke, Aug. 1996.

"39th GE Turbine State–of–the–Art Technology Seminar", Tab 8, "Dry Low $NO_x$ Combustion Systems for GE heavy–Duty Turbines", L. B. Davis, Aug. 1996.

"39th GE Turbine State–of–the–Art Technology Seminar", Tab 9, "GE Gas Turbine Combustion Flexibility", M. A. Davi, Aug. 1996.

"39th GE Turbine State–of–the–Art Technology Seminar", Tab 10, "Gas Fuel clean–Up System design Considerations for GE Heavy–Duty Gas Turbines", C. Wilkes, Aug. 1996.

"39th GE Turbine State–of–the–Art Technology Seminar", Tab 11, "Integrated Control Systems for Advanced Combined Cycles", Chu et al., Aug. 1996.

"39th Ge Turbine State–of–the–Art Technology Seminar", Tab 12, "Power Systems for the 21st Centruy "H" Gas Turbine Combined Cycles", Paul et al., Aug. 1996.

"39th GE Turbine State–of–the–Art Technology Seminar", Tab 13, "Clean Coal and Heavy Oil Technologies for Gas Turbines", D. M. Todd, Aug. 1996.

"39th GE Turbine State–of–the–Art Technology Seminar", Tab 14, "Gas Turbine Conversions, Modifications and Uprates Technology", Stuck et al., Aug. 1996.

"39th GE Turbine State–of–the–Art Technology Seminar", Tab 15, "Performance and Reliability Improvements for Heavy–Duty Gas Turbines, " J.R. Johnston, Aug. 1996.

"39th GE Turbine State–of–the–Art Technology Seminar", Tab 16, "Gas Turbine Repair Technology", Crimi et al, Aug. 1996.

"39th GE Turbine State–of–the–Art Technology Seminar", Tab 17, "Heavy Duty Turbine Operating & Maintgenance Considerations", R. F. Hoeft, Aug. 1996.

"39th GE Turbine State–of–the–Art Technology Seminar", Tab 18, "Gas Turbine Performance Monitoring and Testing", Schmitt et al., Aug. 1996.

"39th GE Turbine State–of–the–Art technology Seminar", Tab 19, "Monitoring service Delivery System and Diagnostics", Madej et al., Aug. 1996.

"39th GE Turbine State–of–the–Art Technology Seminar", Tab 20, "Steam Turbines for Large Power Applications", Reinker et al., Aug. 1996.

"39th GE Turbine State–of–the–Art Technology Seminar", Tab 21, "Steam Turbines for Ultrasupercritical Power Plants", Retzlaff et al., Aug. 1996.

"39th GE Turbine State–of–the–Art Technology Seminar", Tab 22, "Steam Turbine Sustained Efficiency", P. Schofield, Aug. 1996.

"39th GE Turbine State–of–the–Art Technology Seminar", Tab 23, "Recent Advances in Steam Turbines for Industrial and Cogeneration Applications", Leger et al., Aug. 1996.

"39th GE Turbine State–of–the–Art Technology Seminar", Tab 24, "Mechanical Drive Steam Turbines", D. R. Leger, Aug. 1996.

"39th GE Turbine State–of–the–Art Technology Seminar", Tab 25, "Steam Turbines for STAG™Combined–Cycle Power Systems", M. Boss, Aug. 1996.

"39th GE Turbine State–of–the–Art Technology Seminar", Teb 26, "Cogeneration Application Considerations", Fisk et al., Aug. 1996.

"39th GE Turbine State–of–the–Art technology Seminar", Tab 27, "Performance and Economic Considerations of Repowering Steam Power Plants", Stoll et al., Aug. 1996.

"39th GE Turbine State–of–the–Art Technology Seminar", Tab 28, "High–Power–Densigy™Steam Turbine Design Evolution", J. H. Moore, Aug. 1996.

"39th GE Turbine State–of–the–Art Technology Seminar", Tab 29, "Advances in Steam Path Technologies", Cofer, IV, et al., Aug. 1996.

"39th GE Turbine State–of–the–Art Technology Seminar", Tab 30, "Upgradable Opportunities for Steam Turbines", D. R. Dreier, Jr., Aug. 1996.

"39th GE Turbine State–of–the–Art Technology Seminar", Tab 31, "Uprate Options for Industrial Turbines", R. C. Beck, Aug. 1996.

"39th GE Turbine State–of–the–Art Technology Seminar", Tab 32, "Thermal Performance Evaluation and Assessment of Steam Turbine Units", P. Albert, Aug. 1996.

"39th GE Turbine State–of–the–Art Technology Seminar", Tab 33, "Advances in Welding Repair Technology" J. F. Nolan, Aug. 1996.

"39th GE Turbine State–of–the–Art Technology Seminar", Tab 34, "Operation and Maintenance Strategies to Enhance Plant Profitability", MacGillivray et al., Aug. 1996.

"39th GE Turbine State–of–the–Art Technology Seminar", Tab 35, "Generator Insitu Inspections", D. Stanton.

"39th GE Turbine State–of–the–Art Technology Seminar", Tab 36, "Generator Upgrade and Rewind", Halpern et al., Aug. 1996.

"39th GE Turbine State–of–the–Art Technology Seminar", Tab 37, "GE Combined Cycle Product Line and Performance", Chase, et al., Aug. 1996.

"39th GE Turbine State–of–the–Art Technology Seminar", Tab 38, "GE Combined Cycle Experience", Maslak et al., Aug. 1996.

"39th GE Turbine State–of–the–Art Technology Seminar", Tab 39, "Single–Shaft Combined Cycle Power Generation Systems", Tomlinson et al., Aug. 1996.

"Advanced Turbine System Program—Conceptual Design and Product Development", Annual Report, Sep. 1, 1994–Aug. 31, 1995.

"Advanced Turbine Systems (ATS Program) Conceptual Design and Product Development", Final Technical Progress Report, vol. 2—Industrial Machine, Mar. 31, 1997, Morgantown, WV.

"Advanced Turbine Systems (ATS Program), Conceptual Design and Product Development", Final Technical Progress Report, Aug. 31, 1996, Morgantown, WV.

"Advanced Turbine Systems (ATS) Program, Phase 2, Conceptual Design and Product Development", Yearly Technical Progress Report, Reporting Period: Aug. 25, 1993–Aug. 31, 1994.

"Advanced Turbine Systems" Annual Program Review, Preprints, Nov. 2–4, 1998, Washington, D.C. U.S. Department of Energy, Office of Industrial Technologies Federal Energy Technology Center.

"ATS Conference" Oct. 28, 1999, Slide Presentation.

"Baglan Bay Launch Site", various articles relating to Baglan Energy Park.

"Baglan Energy Park", Brochure.

"Commercialization", Del Williamson, Present, Global Sales, May 8, 1998.

"Environmental, Health and Safety Assessment: ATS 7H Program (Phase 3R) Test Activities at the GE Power Systems Gas Turbine Manufacturing Facility, Greenville, SC", Document #1753, Feb. 1998, Publication Date: Nov. 17, 1998, Report No. DE–FC21–95MC31176 –11.

"Exhibit panels used at 1995 product introduction at PowerGen Europe".

"Extensive Testing Program Validates High Efficiency, reliability of GE's Advanced "H" Gas Turbine Technology", Press Information, Press Release, 96–NR14, Jun. 26, 1996, H Technology Tests/pp. 1–4.

"Extensive Testing Program Validates High Efficiency, Reliability of GE's Advanced "H" Gas Turbine Technology, GE Introduces Advanced Gas Turbine Technology Platform: First to Reach 60% Combined—Cycle Power Plant Efficiency", Press INformation, Press Release, Power–Gen Europe '95, 95–NRR15, Advanced Technology INtroduction/pp. 1–6.

"Gas, Steam Turbine Work as Single Unit in GE's Advanced H Technology Combined–Cycle System", Press Information, Press Release, 95–NR18, May 16, 1995, Advanced Technology Introduction/pp. 1–3.

"GE Breaks 60% Net Efficiency Barrier" paper, 4 pages.

"GE Businesses Share Technologies and Experts to Develop State–of–the–Art Products", Press Information, Press Release 95–NR10, May 16, 1995, GE Technology Transfer/pp. 1–3.

"General Electric ATS Program Technical Review, Phase 2 Activities", T. Chance et al., pp. 1–4.

"General Electric's DOE/ATS H Gas Turbine Development" Advanced Turbine Systems Annual Review Meeting, Nov. 7–8, 1996, Washington, D.C., Publication Release.

"H Technology Commercializaation", 1998 MarComm Activity Recommendation, Mar., 1998.

"H Technology", Jon Ebacher, VP, Power Gen Technology, May 8, 1998.

"H Testing Process", Jon Ebacher, VP, Power Gen Technology, May 8, 1998.

"Heavy–Duty & Aeroderivative Products" Gas Turbines, Brochure, 1998.

"MS7001H/M9001H Gas Turbine, gepower.com website for PowerGen Europe" Jun. 1–3 going public Jun. 15, (1995).

"New Steam Cooling System is a Key to 60% Efficiency For GE "H" Technology Combined–Cycle Systems", Press Information, Press Release, 95–NRR16, May 16, 1995, H Technollogy/pp. 1–3.

"Overview of GE's H Gas Turbine Combined Cycle", Jul. 1, 1995 to Dec. 31, 1997.

"Power Systems for the $21^{st}$ Century—"H" Gas Turbine Combined Cycles", Thomas C. Paul et al., Report.

"Power–Gen '96 Europe", Conference Programme, Budapest, Hungary, Jun. 26–28, 1996.

"Power–Gen International", 1998 Show Guide, Dec. 9–11, 1998, Orange County Convention Center, Orlando, Florida.

"Press Coverage following 1995 product announcement", various newspaper clippings relating to improved generator.

"Proceedings of the Advanced Turbine Systems Annual Program review Meeting", vol. 1, "Industrial Advanced Turbine Systems Program Overview", D.W. Esbeck, p. 3–13, Oct., 1995.

"Proceedings of the Advanced Turbine Systems Annual Program Review Meeting", vol. 1, "H Gas Turbine Combined Cycle", J. Corman, p. 14–21, Oct., 1995.

"Proceedings of the Advanced Turbine Systems Annual Program Review Meeting", vol. 1, "Overview of Westinghouse's Advanced Turbine Systems Program", Bannister et al., p. 22–30, Oct., 1995.

"Proceedings of the Advanced Turbine Systems Annual Program Review Meeting", vol. I, "Advanced Turbine Systems Annual Review", William E. Koop, pp. 89–92, Oct., 1995.

"Proceedings of the Advanced Turbine Systems Annual Program Review Meeting", vol. I, "The AGTSR Consortium: An Update", Fant et al., pp. 93–102, Oct., 1995.

"Proceedings of the Advanced Turbine Systems Annual Program Review Meeting", vol. I, "Overview of Allison/AGTSR Interactions", Sy A. Ali, pp. 103–106, Oct., 1995.

"Proceedings of the Advanced Turbine Systems Annual Program Review Meeting", vol. I, "Design Factors far Stable Lean Premix Combustion", Richards et al., pp. 107–113, Oct., 1995.

"Proceedings of the Advanced Turbine Systems Annual Program Review Meeting", vol. I, "Ceramic Stationary as Turbine", M. van Roode, pp. 114–147, Oct., 1995.

"Proceedings of the Advanced Turbine Systems Annual Program Review Meeting", vol. I, "DOE/Allison Ceramic Vane Effort", Wenglarz et al., pp. 148–151, Oct., 1995.

"Proceedings of the Advanced Turbine Systems Annual Program Review Meeting", vol. I, "Materials/Manufacturing Element of the Advanced Turbine Systems Program", Karnitz et al., pp. 152–160, Oct., 1995.

"Proceedings of the Advanced Turbine Systems Annual Program Review Meeting", vol. I, "Land–Based Turbine Casting Initiative", Mueller et al., pp. 161–170, Oct., 1995.

"Proceedings of the Advanced Turbine Systems Annual Program Review Meeting", vol. I, "Turbine Airfoil Manufacturing Technology", Kortovich, pp. 171–181, Oct., 1995.

"Proceedings of the Advanced Turbine Systems Annual Program Review Meeting", vol. I, "Pratt & Whitney Thermal Barrier Coatings", Bornstein et al., pp. 182–193, Oct., 1995.

"Proceedings of the Advanced Turbine Systems Annual Program Review Meeting", vol. I, "Westinhouse Thermal Barrier Coatings", Goedjen et al., pp. 194–199, Oct., 1995.

"Proceedings of the Advanced Turbine Systems Annual Program Review Meeting", vol. I, "High Performance Steam Development", Duffy et al., pp. 200–220, Oct., 1995.

"Proceedings of the Advanced Turbine Systems Annual Program Review Meeting", vol. II, "Lean Premixed Combustion Stabilized by Radiation Feedback and heterogeneos Catalysts", Dibble et al., pp. 221–232, Oct., 1995.

"Proceedings of the Advanced Turbine Systems Annual Program Review Meeting", vol. II, Rayleigh/Raman/LIF Measurements in a Turbulent Lean Premixed Combustor, Nandula et al. pp. 23–248, Oct., 1995.

"Proceedings of the Advanced Turbine Systems Annual Program Review Meeting", vol. II, "Lean Premixed Flames for Low No$_x$ Combustors", Sojka et al., pp. 249–275, Oct., 1995.

"Proceedings of the Advanced Turbine Systems Annual Program Review Meeting", vol. II, "Functionally Gradient Materials for Thermal Barrier Coatings in Advanced Gas Turbine Systems", Banovic et al., pp. 276–280, Oct., 1995.

"Proceedings of the Advanced Turbine Systems Annual Program Review Meeting", vol. II, "Advanced Turbine Cooling, Heat Transfer, and Aerodynamic Studies", Han et al., pp. 281–309, Oct., 1995.

"Proceedings of the Advanced Turbine Systems Annual Program Review Meeting", vol. II, "Life Prediction of Advanced Materials for Gas Turbine Application", Zamrik et al., pp. 310–327, Oct., 1995.

"Proceedings of the Advanced Turbine Systems Annual Program Review Meeting", vol II, "Advanced Combustion Technologies for Gas Turbine Power Plants", Vandsburger et al., pp. 328–352, Oct., 1995.

"Proceedings of the Advanced Turbine Systems Annual Program Review Meeting", vol. II, "Combustion Modeling in Advanced Gas Turbine Systems", Smoot et al., pp. 353–370, Oct., 1995.

"Proceedings of the Advanced Turbine Systems Annual Program Review Meeting", vol. II, "Transfer in a Two–Pass Internally Ribbed Turbine Blade Coolant Channel with Cylindrical Vortex Generators", Hibbs et al. pp. 371–390, Oct., 1995.

"Proceedings of the Advanced Turbine Systems Annual Program Review Meeting", vol. II, "Rotational Effects on Turbine Blade Cooling", Govatzidakia et al., pp. 391–392, Oct., 1995.

"Proceedings of the Advanced Turbine Systems Annual Program Review Meeting", vol. II, "Manifold Methods for Methane Combustion", Yang et al., pp. 393–409, Oct., 1995.

"Proceedings of the Advanced Turbine Systems Annual Program Review Meeting", vol. II, "Advanced Multistage Turbine Blade Aerodynamics, Performance, Cooling, and Heat Transfer", Fleeter et al., pp. 410–414, Oct., 1995.

"Proceedings of the Advanced Turbine Systems Annual Program Review Meeting, vol. II", The Role of Reactant Unmixedness, Strain Rate, and Length Scale on Premixed Combustor Performance, Samuelsen et al., pp. 415–422, Oct., 1995.

"Proceedings of the Advanced Turbine Systems Annual Program Review Meeting", vol. II, "Experimental and Computations Studies of Film Cooling With Compound Angle Injection", Goldstein et al., pp. 423–451, Oct., 1995.

"Proceedings of the Advanced Turbine Systems Annual Program Review Meeting", vol. II, "Compatibility of Gas Turbine Materials with Steam Cooling", Desai et al., pp. 452–464, Oct., 1995.

"Proceedings of the Advanced Turbine Systems Annual Program Review Meeting", vol. II, "Use of a Laser–Induced Fluorescene Thermal Imaging System for Film Cooling Heat Transfer Measurement", M. K. Chyu, pp. 465–473, Oct., 1995.

"Proceedings of the Advanced Turbine Systems Annual Program Review Meeting", vol. II, Effects of Geometry on Slot–Jet Film Cooling Performance, Hyams et al., pp. 474–496 Oct., 1995.

"Proceedings of the Advanced Turbine Systems Annual Program Review Meeting", vol. II, "Steam as Turbine Blade Coolant: Experimental Data Generation", Wilmsen et al., pp. 497–505, Oct., 1995.

"Proceedings of the Advanced Turbine Systems Annual Program Review Meeting", vol. II, "Combustion Chemical Vapor Deposited Coatings for Thermal Barrier Coating Systems", Hampikian et al., pp. 506–515, Oct., 1995.

"Proceedings of the Advanced Turbine Systems Annual Program Review Meeting", vol. II, "Premixed Burner Experiments: Geometry, Mixing, and Flame Structure Issues", Gupta et al., pp. 516–528, Oct., 1995.

"Proceedings of the Advanced Turbine Systems Annual Program Review Meeting", vol. II, "Intercooler Flow Path for Gas Turbines: CFD Design and Experiments", Agrawal et al., pp. 529–538, Oct., 1995.

"Proceedings of the Advanced Turbine Systems Annual Program Review Meeting", vol. II, "Bond Strength and Stress Measurements in THermal Barrier Coatings", Gell et al., pp. 539–549, Oct., 1995.

"Proceedings of the Advanced Turbine Systems Annual Program Review Meeting", vol. II, "Active Control of Combustion Instabilities in Low No$_x$ Gas Turbines", Zinn et al., pp. 550–551, Oct., 1995.

"Proceedings of the Advanced Turbine Systems Annual Program Review Meeting", vol. II, "Combustion Instability Modeling and Aalysis", Santoro et al., pp. 552–559, Oct., 1995.

"Proceedings of the Advanced Turbine Systems Annual Program Review Meeting", vol. II, "Flow and Heat Transfer in Gas Turbine Disk Cavities Subject to Nonuniform External Pressure Field", Roy et al., pp. 560–565, Oct., 1995.

"Proceedings of the Advanced Turbine Systems Annual Program Review Meeting", vol. II, "Haet Pipe Turbine Vane Cooling", Langston et al., pp. 566–572, Oct., 1995.

"Proceedings of the Advanced Turbine Systems Annual Program Review Meeting", vol. II, "Improved Modeling Techniques for Turbomachinery Flow Fields", Lakshminarayana et al., pp. 573–581, Oct., 1995.

"Proceedings of the Advanced Turbine Systems Annual Program Review Meeting", vol. II, "Advanced 3D Inverse Method for Designeng Turbomachine Blades", T. Dang, p. 582, Oct., 1995.

"Proceddings of the Advanced Turbine Systems Annual Program Review Meeting", "ATS and the Industries of the Future", Denise Swink, p. 1, Nov., 1996.

"Proceedings of the Advanced Turbine Systems Annual Program Review Meeting", "Gas Turbine Association Agenda", William H. Day, pp. 3–16, Nov., 1996.

"Proceedings of the Advanced Turbine Systems Annual Program Review Meeting", "Power Needs in the Chemical Industry", Keith Davidson, pp. 17–26, Nov., 1996.

"Proceedings of the Advanced Turbine Systems Annual Program Review Meeting", "Advanced Turbine Systems Program Overview", David Esbeck, pp. 27–34, Nov., 1996.

"Proceedings of the Advanced Turbine Systems Annual Program Review Meeting", "Westinghous's Advanced Turbine Systems Program", Gerard McQuiggan, pp. 35–48, Nov., 1996.

"Proceedings of the Advanced Turbine Systems Annual Program Review Meeting", "Overview of GE's H Gas Turbine Combined Cycle", Cook et al., pp. 49–72, Nov., 1996.

"Proceedings of the Advanced Turbine Systems Annual Program Review Meeting", "Allison Advanced Simple Cycle Gas Turbine System", William D. Weisbrod, pp. 73–94, Nov., 1996.

"Proceedings of the Advanced Turbine Systems Annual Program Review Meeting", "The AGTSR Industry–University Consortium", Lawrence P. Golan, pp. 95–110, Nov., 1996.

"Proceedings of the Advanced Turbine Systems Annual Program Review Meeting", "$NO_x$ and CO Emissions Models for Gas–Fired Lean–Premixed Combustion Turbines", A. Mellor, pp. 111–122, Nov., 1996.

"Proceedings of the Advanced Turbine Systems Annual Program Review Meeting", "Methodologies for Active Mixing and Combustion Control", URI Vandsburger, pp. 123–156, Nov., 1996.

"Proceedings of the Advanced Turbine Systems Annual Program Review Meeting", "Combustion Modeling in Advanced Gas Turbine Systems", Paul O. Hedman, pp. 157–18, Nov., 1996.

"Proceedings of the Advanced Turbine Systems Annual Program Review Meeting", "Manifold Methods for Methane Combustion", Stephen B. Pope, pp. 181–199, Nov., 1996.

"Proceedings of the Advanced Turbine Systems Annual Program Review Meeting", "The Role of Rectant Unmixedness, Strain Rate, and Length Scale on Premixed Combustor Performance", Scott Samuelsen, pp. 189–210, Nov., 1996.

"Proceedings of the Advanced Turbine Systems Annual Program Review Meeting", "Effect of Swirl and Momentum Distribution on Temperature Distribution in Premixed Flames", Ashwani K. Gupta, pp. 211–232, Nov., 1996.

"Proceedings of the Advanced Turbine Systems Annual Program Review Meeting", "Combustion Instability Studies Application to Land–Based Gas Turbine Combustors", Robert J. Santoro, pp. 233–252.

"Proceedings of the Advanced Turbine Systems Annual Program Review Meeting", Active Control of Combustion Instabilities in Low $NO_x$ Turbines, Ben T. Zinn, pp. 253–264, Nov., 1996.

"Proceedings of the Advanced Turbine Systems Annual Program Review Meeting", "Life Prediction of Advanced Materials for Gas Turbine Application," Sam Y. Zamrik, pp. 265–274, Nov., 1996.

"Proceedings of the Advanced Turbine Systems Annual Program Review Meeting", "Combustion Chemical Vapor Deposited Coatings for Thermal Barrier Coating Syatems", W. Brent Carter, pp. 275–290, Nov., 1996.

"Proceedings of the Advanced Turbine Systems Annual Program Review Meeting", "Compatibility of Gas Turbine Materials with Steam Cooling", Vimal Desai, pp. 291–314, Nov., 1996.

"Proceedings of the Advanced Turbine Systems Annual Program Review Meeting", "Bond Strength and Stress Measurements in Thermal Barrier Coatings", Maurice Gell, pp. 315–334, Nov., 1996.

"Proceedings of the Advanced Trubine Systems Annual Program Review Meeting", "Advanced Multistsge Turbine Blade Aerodynamics, Performance, Cooling and Heat Transfer", Sanford Fleeter, pp. 335–356, Nov., 1996.

"Proceedings of the Advanced Turbine Systems Annual Program Review Meeting", "Flow Characteristics of an Intercooler System for Power Generating Gas Turbines", Ajay K. Agrawal, pp. 357–370, Nov., 1996.

"Proceedings of the Advanced Turbine Systems Annual Program Review Meeting", "Improved Modeling Techniques for Turbomachinery Flow Fields", B. Lakshiminarayana, pp. 371–392, Nov., 1996.

"Proceedings of the Advanced Turbine Systems Annual Program Review Meeting", "Development of an Advanced 3d & Viscous Aerodynamic Design Method for Turbomachine Components in Utility and Industrial Gas Turbine Applications", Thong Q. Dang, pp. 393–406, Nov., 1996.

"Proceedings of the Advanced Turbine Systems Annual Program Review Meeting", "Advanced Turbine Cooling, Haet Transfer, and Aerodynamic Studies", Je–Chin Han, pp. 407–426, Nov., 1996.

"Proceedings of the Advanced Turbine Systems Annual Program Review Meeting", "Heat Transfer in a Two–Pass Internally Ribbed Turbine Blade Coolant Channel with Vortex Generators", S. Acharva, pp. 427–466.

"Proceedings of the Advanced Turbine Systems Annual Program Review Meeting", "Experimental and Computational Studies of Film Cooling with Compound Angle Injection", R. Goldstein, pp. 447–460, Nov., 1996.

"Proceedings of the Advanced Turbine Systems Annual Program Review Meeting", "Study of Endwall Film Cooling with a Gap Leakage Using a Thermographic Phosphor Fluorescence Imaging System", Mingking K. Chyu, pp. 461–470, Nov., 1996.

"Proceedings of the Advanced Turbine Systems Annual Program Review Meeting", "Steam as a Turbine Blade Coolant: External Side Heat Transfer", Abraham Engeda, pp. 471–482, Nov., 1996.

"Proceedings of the Advanced Turbine Systems Annual Program Review Meeting", "Flow and Heat Transfer in Gas Turbine Disk Cavities Subject to Nonuniform External Pressure Firld", Ramendra Roy, pp. 483–498, Nov., 1996.

"Proceedings of the Advanced Turbine Systems Annual Program Review Meeting", "Closed–Loop Mist/Stream Cooling for Advanced Turbine Systems", Ting Wang, pp. 499–512, Nov., 1996.

"Proceedings of the Advanced Turbine SYstems Annual Program Review Meeting", "Heat Pipe Turbine Vane Cooling", Langston et al., pp. 513–534, Nov., 1996.

"Proceedings of the Advanced Turbine Systems Annual Program Review Meeting", "EPRI's Combustion Turbine Program: Status and Future Directions", Arthur Cohn, pp. 535,–552, Nov., 1996.

"Proceedings of the Advanced Turbine Systems Annual Program Review Meeting", "ATS Materials Support", Michal Karnitz, pp. 553–576, Nov., 1996.

"Proceedings of the Advanced Turbine Systems Annual Program Review Meeting", "Land Based Turbine Casting Initiative", Boyd A. Mueller, pp. 577–592, Nov., 1996.

"Proceedings of the Advanced Turbine Systems Annual Program Review Meeting", "Turbine Airfoil Manufacturing Technology", Charles S. Kortovich, pp. 593–622, Nov., 1996.

"Proceedings of the Advanced Turbine Systems Annual Program Review Meeting", "Hot Corrosion Testing of TBS's", Norman Bornstein, pp. 623–631, Nov., 1996.

"Proceedings of the Advanced Turbine Systems Annual Program Review Meeting", "Ceramic Stationary Gas Turbine", Mark van Roode, pp. 633–658, Nov., 1996.

"Proceedings of the Advanced Turbine Systems Annual Program Review Meeting", "Western European Status of Ceramics for Gas Turbines", Tibor Bornemisza, pp. 659–670, Nov., 1996.

"Proceedings of the Advanced Turbine Systems Annual Program Review Meeting", "Status of Ceramic Gas Trubines in Russia", Mark van Roode, p. 571, Nov., 1996.

"Staus Report: The U.S. Department of Energy's Adavnced Trubine systems Program", facsimile dated Nov. 7, 1996.

"Testing Program Results Validate GE's H Gas Turbine – High Efficiency, Low Cost of Electricity and Low Emissions", Roger Schonewald and Patrick Marolda, (no date available).

"Testing Program Results Validate GE's H Gas Turbine – High Efficiency, Low Cost of Electricity and Low Emissions", Slide Presentation –working draft, (no date available).

"The Next Step In H . . . For Low Cost Per kW–Hour Power Generation", LP–1 PGE '98.

"Utility Advanced Turbine System (ATS) Technology Readiness Testing and Pre–Commercialization Demonstration", Document #486040, Oct. 1–Dec. 31, 1996, Publication Date, Jun. 1, 1997, Report Numbers: DOE/MC/31176—5628.

"Utility Advanced Turbine System (ATS) Technology Readiness Testing —Phase 3", Document #666274, Oct. 1, 1996–Sep. 30, 1997, Publication Date, Dec. 31, 1997, Report Numbers: DOE/MC/31176—10.

"Utility Advanced Turbine System (ATS) Technology Readiness Testing and Pre–Commercial Demonstration, Phase 3", Document #486029, Oct. 1–Dec. 31, 1995, Publication Date, May 1, 1997, Report Numbers: DOE/MC31176—5340.

"Utility Advanced Turbine System (ATS) Technology Readiness Testing and Pre–Commercial Demonstration – Phase 3", Document #486132, Apr. 1–Jun. 30, 1976, Publication Date, Dec. 31, 1996, Report Numbers: DOE/MC/31176—5660.

"Utility Advanced Turbine System (ATS) Technology Readiness Testing and Pre–Commercial Demonstartion — Phase 3", Document 190 587906, Jul. 1–Sep. 30, 1995, Publication Date, Dec. 31, 1995, Report Numbers: DOE/MC/31176—5339.

"Utility Advanced Turbine System (ATS) Technology Readiness Testing and Pre–Commercial Demonstration" Document #666277, Apr.1–Jun. 30, 1997, Publication Date, Dec. 31, 1997, Report Numbers: DOE/MC/31176—8.

"Utility Advanced Turbine System (ATS) Technology Readiness Testing and Pre–Commercialization Demonstration" Jan. 1–Mar. 31, 1996, DOE/MC/31176—5338.

"Utility Advanced Turbine System (ATS) Technology Readiness Testing: Phase 3R", Document #756552, Apr. 1–Jun. 30, 1999, Publication Date, Sep. 1, 1999, Report Numbers: DE—FC21–95MC31176–23.

"Utililty Advanced Turbine System (ATS) Technology Readiness Testing.", Document #656823, Jan. 1–Mar. 31, 1998, Publication Date, Aug. 1, 1998, Report No. DOE/MC/31176–17.

"Utility Adbanced Turbine Systems (ATS) Technology Readiness Testing and Pre–commercial Demonstration", Annual Technical Progress Report, Reporting Period: Jul. 1, 1995–Sep. 30, 1996.

"Utility Advanced Turbine Systems (ATS) Technology Testing", Phase 3R, Annual Technical Progress Report, Reporting Period: Oct. 1, 1997–Sep. 30, 1998.

"Utility Advanced Turbine Systems (ATS) Technology Readiness Testing", Document #750405, Oct. 1–Dec. 30, 1998, Publication Date: May, 1, 1999, Report No.: DE–FC21–95MC31176–20.

"Utility Advanced Turbine Systems (ATS) Technology Readiness Testing", Document #1348, Apr. 1–Jun. 29,1998, Publication Date Oct. 29, 1998, Report No. DE–FC21–95, C31176–18.

"Utility Advanced Turbine Systems (ATS) Technology Readiness Testing—Phase3", Annual Technical Progress Report, Reporting Period: Oct. 1, 1996–Sep. 30, 1997.

"Utility Advnced Turbine Systems (ATS) Technology Readiness Testing and Pre–commercial Demonstration", Quarterly Report, Jan. 1–Mar. 31, 1997, Document #666275, Report No.: DOE/MC/31176–07.

"Proceedings of the 1997 Advanced Turbine Systems", Annual Program Review Meeting, Oct. 28–29, 1997.

* cited by examiner

US 6,378,386 B1

SURFACE CLEANLINESS MEASUREMENT PROCEDURE

This application is a division of application Ser. No. 09/669,574 filed Sep. 26, 2000, the entire content of which is hereby incorporated by reference in this application.

This invention was made with Government support under Government contract No. DE-FC21-95-MC31176 awarded by the Department of Energy. The Government has certain rights in this invention.

BACKGROUND OF THE INVENTION

The invention relates to a procedure and tools for conducting a robust, quantitative measurement of surface cleanliness for field installation, factory fabrication, and assembly of mechanical systems such as power plant equipment. More specifically, the invention provides a quantification of the qualitative white glove test often used by cleanliness inspectors.

Surface particulate contamination is a well-known source of mechanical system failures. Particulate contamination can cause abrasion at the interface between moving parts, contamination of fluids flowing through the system and erosion of structures in high velocity fluid flow path(s) and/or create deposits that either reduce desired flows or insulate against desired heat transfer. While the provision of filters and the like can control the flow of particulate contaminates into a system during operation, in some systems the presence of particulate contaminates on parts during assembly can substantially contribute to particulate accumulation in the field and the resultant risk of poor performance and/or reduced component operating life. Moreover, filters are always specified with effectiveness, which means that a small percentage of undesirable particles will always pass through.

A variety of approaches to determine surface cleanliness are known and used for various components and surfaces. However, none of those approaches deal with directly measuring the presence and amount of particulate on the surface of a large component during factory assembly. Instead, these techniques focus either on measurement of particulate concentration in fluids used to wash parts or on determining the presence of organic films. The fluid concentrations are usually determined using light attenuation or refraction, often using laser beams. The organic films are determined by creating a water film on the surface and determining the formation of droplets or breakup of fluid films into rivulets, or the organic film thickness is determined by refraction of light shined at the film. The fluid based approaches cannot be adapted for practical, economic use on a mechanical assembly floor and the second mentioned technique is not relevant since the particles, not an organic film, is at issue.

In another known approach, surface replicas are used. With such replicas, the surface to be sampled is covered with either an adhesive tape or is covered with a curable material, which subsequently replicates the surface topography while also capturing loosely held surface particulate contamination. The surface is then scanned manually or with sophisticated optical recognition software to count numbers of particles and sizes. This approach is indeed used scientifically but it cannot give instantaneous results on the factory floor and in most cases would be considered prohibitively expensive. Moreover, the sample area is of necessity, exactly equal to the size of the removed sample. No amplification can be obtained this way. In other words, it is not possible to sample a larger area than that of the sampling device itself.

BRIEF SUMMARY OF THE INVENTION

The invention provides a special procedure using a set of specialized equipment to quantify the particulate contamination of a component surface. In a preferred embodiment of the invention, the contamination can be amplified to provide for a more accurate reading, by sampling a larger component area then the area of the sampling device itself. With the sampling devices of the invention, a measurement is provided that has visual meaning to the operator making it and provides a convenient archival form of the contamination sample for later process audit, if necessary or desirable.

According to the well-known white glove test, an inspector wears a bright white glove and wipes a glove finger or hand across the target surface for some distance and then observes the glove where it touched the surface. The inspector then makes an arbitrary decision about whether the removed contamination is sufficiently low as to not require a recleaning of the surface. The invention provides equipment and procedures to quantify this conventional white glove test. In an embodiment of the invention, a bright white cloth swatch is rubbed on a known clean surface similar in surface roughness to the surface that is to be sampled. The surface wipe is preferably accomplished by securing the swatch to a tool adapted to be grasped by the operation and swiped on a target surface area with a generally repeatable amount of pressure. Most preferable the target area is defined, and limited by a mask. The effectively still clean swatch or smear is then measured for its reflectivity (brightness) using a reflectivity instrument. The smear is then rubbed on the surface to be tested to collect particulate contamination and the reflectivity is again measured. The loss of reflectivity is then related, for example, through imperical calibration, to the amount of contamination that was transferred to the smear in the second rubbing.

In another embodiment, a reflectivity instrument is calibrated based on the reflectivity of the clean surface rubbed swatch so that only a single rub of each swatch thereafter, on the part to be tested, is required.

In yet a further embodiment of the invention, a contamination key is provided illustrating the appearance of the cloth wipe or swatch exhibiting different amounts of particulate contamination so that following a test swipe of the component, the swatch can be compared to the key to visually approximate the level of contamination.

DETAILED DESCRIPTION OF THE INVENTION

The surface cleanliness measurement technique embodying the invention is a quantitative adaptation of the "white glove" technique, which has been used throughout history to spot check surface cleanliness. The invention provides a robust, quantitative measurement of surface cleanliness for field installation, factory fabrication and assembly of mechanical equipment. The technique is applicable to a variety of manufacturing procedures such as checking for cleanliness on close mating components to ensure debris does not interfere with the fit-up. It can also be used to monitor cleanliness of manufactured components and to monitor cleanliness compliance in clean rooms.

The invention proposes to measure surface cleanliness by sampling a prescribed area of a surface of the component and determining the amount of particulate contamination transferred to the sampling device. According to a preferred embodiment of the invention, the sampling protocol specifies certain features of the swiping process important to accurately quantify particle contamination, including sampling device area in contact with the target surface, the area sampled by the sampling device, the force of the wipe, the uniformity of pressure distribution, and the amount of wiping done to collect the sample. The amount of contamination is then quantified by a calibration technique that relates the reduction in light reflectance of the cloth sample and the mass of the dirt type that was collected on the cloth sample.

A key to effective sampling is to properly mount the debris-collecting device on a tool in such a way that the contamination is transferred to the debris-collecting device as much as possible. Two basic tools are provided in an exemplary embodiment of the invention to perform the contamination measurement. The first tool is a hand tool, which carries the debris collecting material or smear while the target area is wiped for contamination. The hand tool is preferably equipped with a spring that is compressed during wiping to apply a known force during the wipe of about 170 g. The second tool is a pole tool for sampling, e.g., the inside of a pipe. The area sampled inside the pipe is determined by wiping around the complete inner circumference over a known axial distance. Providing indicia along at least a portion of the length of the pole allows the axial distance of the swipe to be monitored. Like the hand tool, the pole tool is equipped with a spring to apply a uniform force during the wipe. In a presently preferred exemplary embodiment, the spring component for both the hand tool and the pole tool is a layer of foam interposed between the body of the tool and the smear to more uniformly distribute the wiping pressure, as described in greater detail below.

Figure 1:
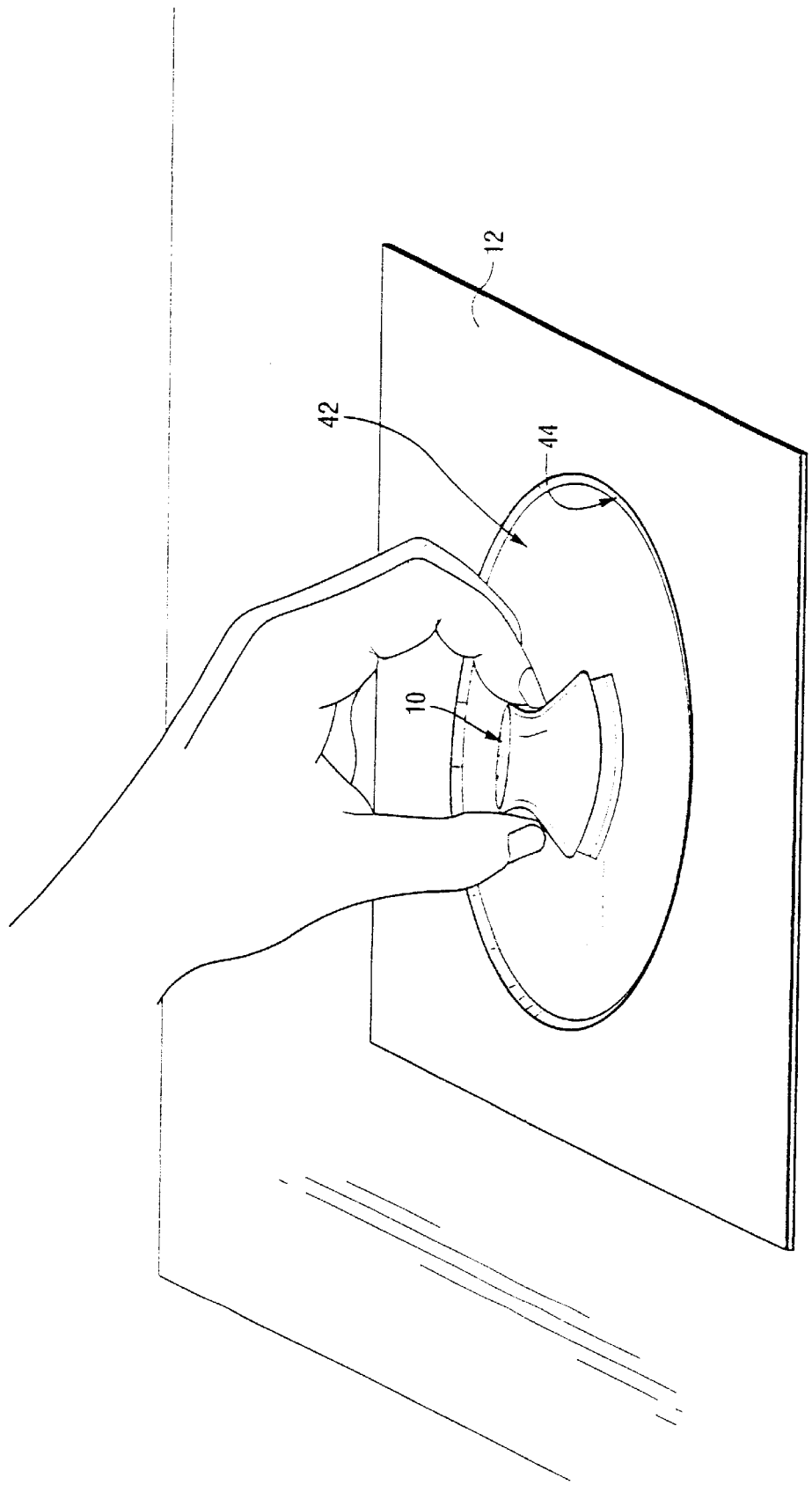
FIG. 1 is a perspective view showing a cleanliness measurement procedure embodying the invention.
Figure 2:
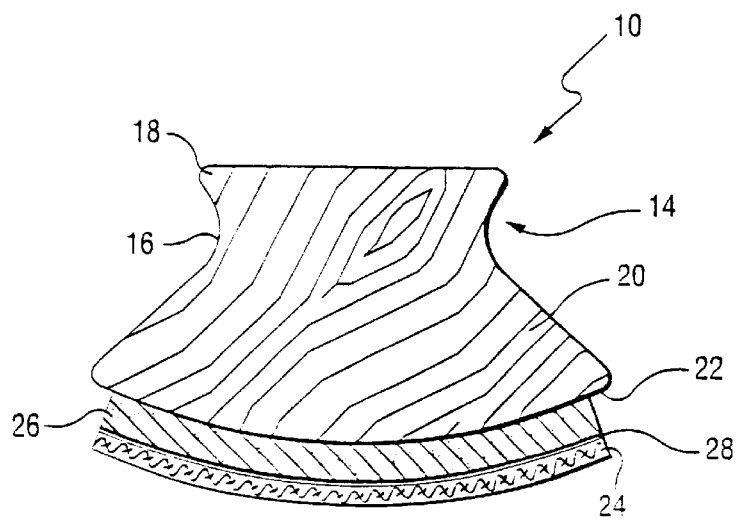
FIG. 2 is a schematic cross sectional view of an exemplary cleanliness measurement tool embodying the invention.

An example of a hand tool that may be used for swiping a target surface is a wooden drawer pull having approximately 2 inch diameter major surface to which a layer of foam is applied. This tool provides a simplified approach with which a firm but not excessive force can be used to obtain the smear sample. In FIG. 1, a hand tool 10 such as an adapted drawer pull is shown during a contamination collection procedure. As illustrated, a mask 12 is preferably provided, as described in greater detail below, to limit the area that can be swiped with the hand tool. A schematic cross sectional view of this exemplary hand tool is shown in FIG. 2. As illustrated, the hand tool includes a hand grip portion 14 which in the case of a drawer pull is composed of the reduced diameter neck 16 of the drawer pull and the base 18, and an operative portion or main body 20 including an operative surface 22 to which the smear 24 is mounted.

As mentioned above, in the presently preferred embodiment, a spring, such as a layer of foam 26 is interposed between the main body 20 of the tool 10 and the smear 24. In the presently preferred embodiment, the layer of foam has a thickness of about ⅛ to ¼ inch. The foam is preferably fixedly secured to the hand tool main body for example with an adhesive suitable for bonding foam to the material, e.g. wood, plastic, or metal, of the hand tool main body 20. The smear 24 is preferably detachably coupled to the distal surface of the foam. In an exemplary embodiment, an adhesive layer 28 is provided on the smear that is releasable and reapplyable so that the smear can be releasably attached to a supply sheet, removed from the supply sheet and adhered to the foam of the tool and then removed from the tool and applied to an archival sheet. Suitable adhesives that will releasably attach the smear to the foam so that the smear remains in place during the swiping operation but which is detachable from the foam and maintains sufficient adhesion to be applied to an archival sheet are known and suitable such adhesives can be readily identified by those skilled in the art.

As an alternative to providing a resilient material on the hand tool, the smear can be supplied with a resilient backing adhered thereto so that the swipe and resilient backing are together applied and removed from the hand tool.

Figure 3:
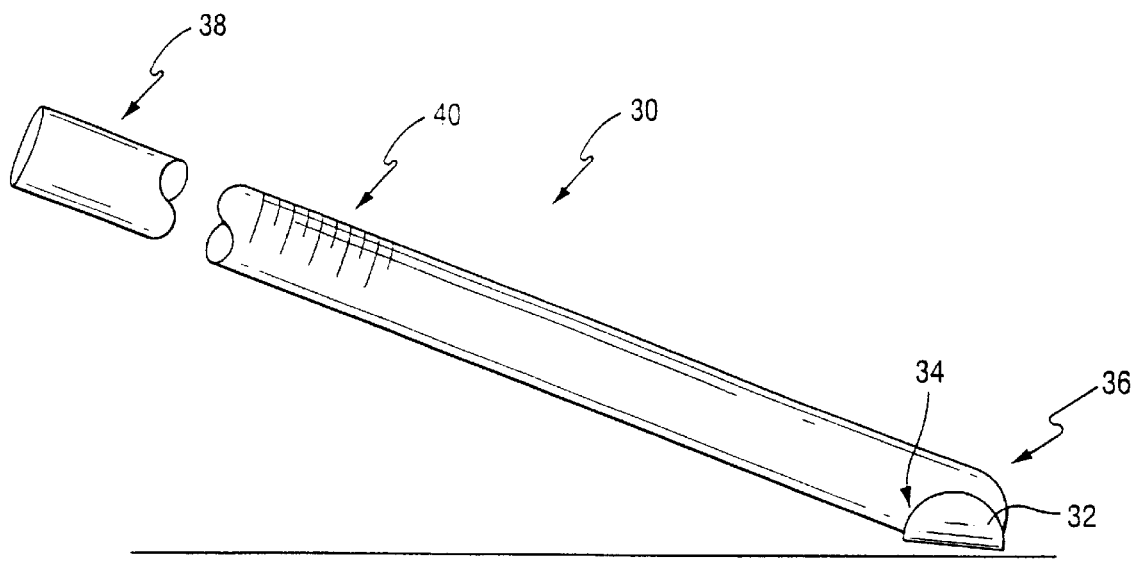
FIG. 3 is an elevational view of another cleanliness measurement tool embodying the invention.

As schematically illustrated in FIG. 3, the pole tool is preferably in the form of an elongated pole component or dowel 30 or, e.g., wood, plastic or metal material, having a diameter of at least about ½ inch and a length on the order of from about 8 inches to about 4 feet long. A smear 32 is preferably adhered to a resilient material (not shown in FIG. 3) such as a foam layer (not shown) provided on an operative surface 34 of a main body 35 of the tool, at the distal end 36 thereof. The proximal end of the pole tube is used as a hand grip portion 38. As noted above, the pole tool may have indicia 40 along its length to indicate the depth of insertion into a pipe or tube and so that the operator can swipe the pipe interior through a prescribed axial length.

Accordingly, to conduct a contamination sampling, a tool is selected for receiving the smear and swiping a target region of the component surface. In one exemplary embodiment, typified by the hand tool 10 illustrated in FIG. 2, the sampling tool has an operative face 22 generally corresponding to but slightly greater in diameter than the smear 24 to ensure substantially full surface contact of the smear with the surface to be sampled. As also explained above, the tool operative surface is also preferably resilient to control and increase the contact area between the smear and the target surface. In a preferred embodiment, then, the smear is mounted on a small, 2 inch outer diameter tool face which is generally continuously curved and preferably approximately spherically convex. As noted above, to control and increase the contact area between the smear and the target surface, the tool has a thin layer of foam or other resilient material fixedly secured on the tool face, under the smear.

In a preferred embodiment, the smear is a bright white circular cloth disk 24,32 having a diameter of about 1 to 2½ inches, more preferably about 1½ to 2 inches and most preferably about 1¾ inches in diameter. To securely but removably secure the cloth to the tool 10,30, the backside of the cloth swatch (hereafter referred to as a smear) has a multiple-use contact adhesive 28 applied thereto that is used to selectively adhere the smear to a supply sheet, to the sampling tool, and then to a convenient archival form for later process or audit, should that be necessary. Suitable smears of 1¾ inch diameter having a multiple-use contact adhesive on one side can be obtained from DA Services, Inc. Defense Apparel, 247 Addison Road, Windsor, Conn. 06095.

To limit the area to be sampled to a prescribed area, the area to be sampled is preferably masked with a clean and stiff but flexible sheet of material 12 such as Teflon into which a sampling area 42 has been cut. The sheet stock from which the mask is formed preferably has a thickness on the order of about 1/16 of an inch with a known open area therein used as a guide for sampling. In an exemplary embodiment, a circular hole of approximately 6 inches diameter (15.24 cm) and having a chamfered edge 44 is formed in the sheet stock thereby defining the sampling hole to limit the sampling to a controlled region of known area. Either the hand tool 10 or the pole tool 30 can sample the area defined by the mask 12.

To avoid removal of particulate contamination from the smear, according to a preferred wiping procedure, the forward edge of the smear tool is lifted as it is moved in ever increasing circles from the center outward. Moreover, advantageously, as the smear tool is moved it is so rotated into the direction of motion as to provide a fresh surface of the smear to pick up contamination. As the wiping trajectory approaches the inner, chamfered edge of the mask, the tool is so tilted that the outside edge rides up slightly over the lip of the mask while the wiping motion is tangential to the inner edge. This overlap enables the capture of any material inadvertently rubbed out onto the mask. Meanwhile, the tangential motion minimizes the tendency to rub contamination from the sampled area out under the mask.

Two wipes of the surface are generally sufficient to capture substantially all the surface contamination on the smear. A second wipe will not only collect residue from the first wiping but will also smear the contamination around the cloth to make a more uniform darkening of the smear. According to the preferred embodiment of the invention, a sampling area is not rubbed more than 3 times because of the effects of pushing the contamination from the surface to the interior of the cloth structure. Also, the additional rubbing may degrade the cloth sampling surface by abrasion. These adverse effects on the ultimate reflectivity measurements can be discounted, however, by consistently following a selected procedure exactly each time. It is clear that the accuracy, repeatability and reproducibility of the cleanliness measurement will largely depend upon the sampling being carried out using a prescribed procedure, that is a prescribed number of wipes and prescribed wipe pattern on a prescribed surface area, each time the measurement has carried out.

The swiping procedure, the smear and the target surface may be pretreated to facilitate the removal of contamination to evaluate the same. For example, it may be beneficial to precoat the smear with a clear and somewhat tacky coating to enable it to hold larger amounts of loose particulate matter. That coating may be applied either initially or after the first wipe procedure or in advance of each wipe procedure. It may also be of benefit in select testing procedures to spray the target surface with a clear liquid cleaner to help release contamination from the target surface and transfer it to the smear. It is also to be appreciated that the presence of any remnant oil film from the target surface may require a re-calibration with that same level of oil film since the oil, even without particulate will be likely to reduce the smear brightness itself. As an alternative, the smear can be soaked to vaporize any organic material leaving only the particulate residue to reduce reflectivity. These potential enhancements to the contaminant removal will ultimately depend, at least in part, upon the purpose for the surface contamination evaluation. When the testing procedure is provided for the purpose of evaluating the amount of debris that may, in use, be released from the surface and collected at deposition points within the apparatus in the field, then it is desirable for the swipe test to be indicative of the particulate material that may be removed from the surface and redeposited during normal use of the component.

The amount of contamination picked up by the smear is measured by comparing the reduction in smear reflectivity to a known amount of contamination in the area being sampled. The reflectivity meter and sensor are a commercial system, set up to operate with a blue filter where the specimen (smear) is pressed against the face of the sensor head. The sensor head has a 3/4 inch hole in its distal end and contains both the light source and the photomultiplier, which illuminates and measures reflectance from objects placed against the 3/4 inch hole. One example of the device described is a Photovolt Model 577 and can be purchased from UMN Electronics—Photovolt Division, 6911 Hillsdale Court, Indianapolis, Tenn. 46250.

An exemplary Smear Sampling Technique includes the following steps:

1. Measure unused smear reflectivity once or twice to verify that the smear is new. Record the actual reflectivity value.
2. Mount smear on a tool by using tweezers to transfer the smear from its paper folder to the wiping tool.
3. Conduct a pre-wipe to "condition" the smear for its initial loss of reflectivity. The conduct of a pre-wipe and of a sample wipe is identical. The smear is wiped completely over the target surface twice, controlling the applied force where it is measurable (hand tool). For the hand tool, it is recommended that the wipe start at the center of the masked area and gradually spiral outward to slightly overlap the mask. Each pass should take about 5 seconds, so a complete wipe will take a bit over 10 seconds.
4. Using only tweezers, transfer the smear to its paper folder.
5. Make a 5-point measurement of reflectivity, being sure to move the measurement area 1/4 inch off the smear center in each direction. Record the measurements.
6. Store the smear for later examinations and comparisons.
7. An unused smear should be saved (about once per batch of surface measurements) to serve as controls for later remeasurements.

Figure 4:
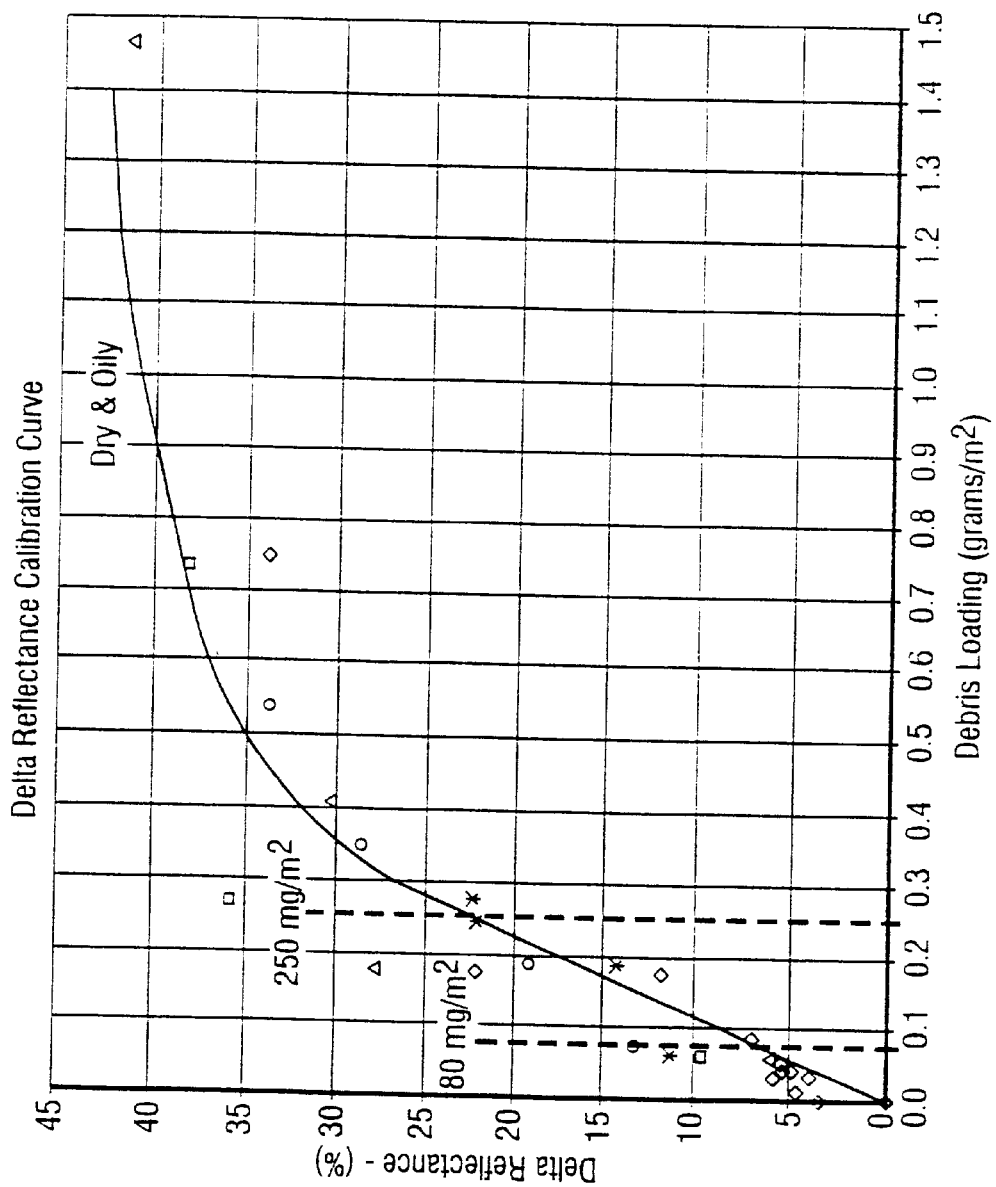
FIG. 4 is a delta reflectance calibration curve.

An example of a calibration procedure procedure is as follows: a sample of the particulate material to be collected is placed on a weigh paper in a laboratory balance to obtain its gross weight. The sample is then distributed within the area of the mask placed on the calibration target surface. The empty weigh paper is then reweighed to get the tare weight. Then, a sample wiping procedure is performed, as described above, and a reflectivity measurement is performed, as described above. Results are graphed as the reduction in (delta) reflectivity (value of the smear after the pre-wipe to after the sample) as a function of the mass loading ($gm/m^2$) of contaminant placed inside the masked area. An example of a calibration curve is provided as FIG. 4.

Figure 5:
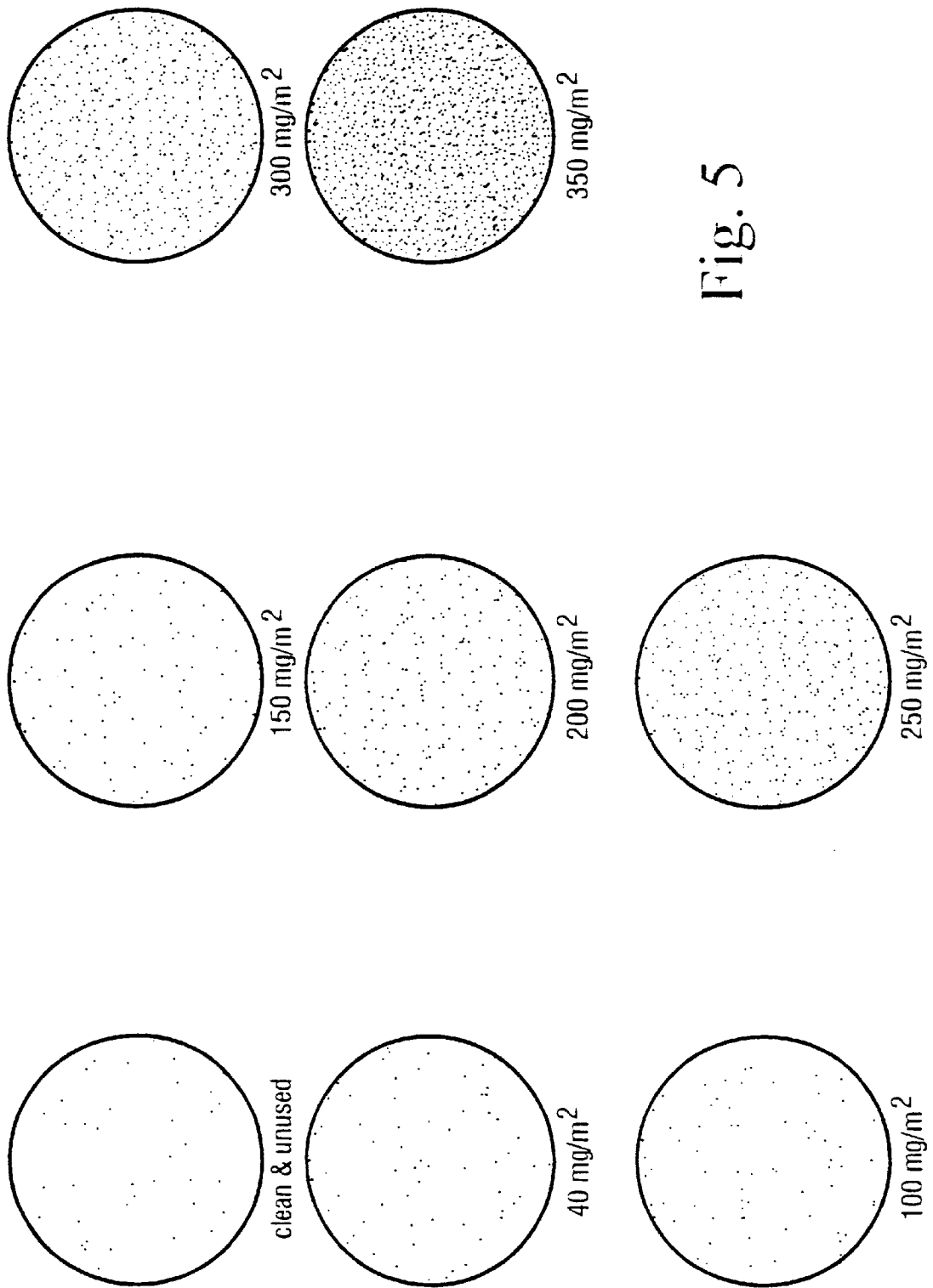
FIG. 5 is a particulate contamination key embodying the invention.

As an alternative to measuring the reflectivity of each smear following the surface wipe, a particulate contamination key, as illustrated by way of example in FIG. 5, can be prepared to show the visual appearance of smears that have been used to wipe surfaces having various known mass loading of contamination. Then, following a wiping procedure, the smear can be visually compared to the key to determine the approximate surface contamination of the component being tested.

As noted above, the cloth smears that are preferably used in the surface contamination evaluation process of the invention are available commercially, but they have been used heretofore to manually wipe surfaces suspected of having radioactive material on them. After wiping, the smears have conventionally been placed under radiation detectors to measure the radioactivity. The smear cloths are conventionally supplied adhered to wax paper folders to enabling labeling, sample protection and archiving as is the case with the preferred embodiment of the invention. As noted, however, the smear cloths have been manually held to swipe testing surfaces and no provision has been made to improve collection efficiency by using a special rubbing tool as disclosed hereinabove.

It is to be appreciated that the invention has several benefits for use on the factory floor. The stain or contamination of the smear is very visual to the operator and subsequent measurement is quite understandable without technical training. Also, the reflectivity measurement can be made on the factory floor within minutes of the sample smear being wiped on the target surface. This is advantageous in effective implementation of the technique under the time pressures of a major manufacturing and assembling operation. It also minimizes the risk of smear contamination or accumulated particle loss during transport to a remote detection site. Because the operator can both sample and measure himself, there is an increased likelihood that the process will be regularly used and will consequently reinforce the operator's awareness of cleanliness requirements. As noted above, the masked area is for example about 6 inches which is substantially larger than the diameter of the swatch which is preferably about 1.75 inches. This means that the sampled area is $(6/1.75)^2$ or almost 12 times larger than the area of the swatch. This provides a sample concentration that is an order of magnitude improvement over using replicas, even if the smear collection was only 90% effective. This increases the likelihood that even low levels of particulate contamination can be accurately detected and measured.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of measuring surface cleanliness comprising:
   providing a sampling device comprising:
      a main body portion;
      a hand grip portion fixedly disposed with respect to said main body portion so that motion of said hand grip portion effects motion of said main body portion;
      a debris collecting component detachedly coupled to an operative surface of said main body portion, whereby said debris collecting component can be disposed in contact with and moved relative to a target surface, and thereafter detached from said main body portion for at least one of storage and evaluation, wherein said operative surface is convexly curved and wherein said debris collecting component is detachably secured to said operative surface with a reusable adhesive layer;
   wiping a prescribed area of a target surface with said sampling device; measuring a reflectivity of a surface of said sampling device to determine a cleanliness of the target surface.

2. A method as in claim 1, wherein said step of wiping is repeated at least once with the same debris collecting component before said measuring step.

3. A method as in claim 1, further comprising providing a mask component having an opening defined therein to define said prescribed area of said target surface for being wiped with said sampling device and wherein said step of wiping comprises wiping an area of the target surface delineated by said opening in said mask component.

4. A method as in claim as in claim 3, wherein said step of providing a mask component comprises providing a mask component having a beveled inner peripheral edge defining said opening.

5. A method as in claim 1, further comprising detachably securing said smear component to said tool.

6. A method of measuring surface cleanliness comprising:
   providing a sampling device;
   wiping a prescribed area of a target surface with said sampling device;
   visually comparing a debris loaded surface of said sampling device to a visual particulate contamination key showing exemplary debris loaded surfaces to determine a cleanliness of the target surface, further comprising providing a mask component having an opening defined therein to define said prescribed area of said target surface for being wiped with said sampling device and wherein said step of wiping comprises wiping an area of the target surface delineated by said opening in said mask component, wherein an inner peripheral edge of said mask component defining said opening is beveled.

7. A method as in claim 6, wherein said step of wiping is repeated with a same sampling surface of the sampling device at least once before said comparing step.

8. A method as in claim 6, wherein said sampling device comprises a smear component secured to a tool.

9. A method as in claim 8, further comprising detachably securing said smear component to said tool.

10. A method of measuring surface cleanliness comprising:
    provide a sampling device;
    providing a mask component having an opening defined therein to define a prescribed area of a target surface for being wiped with said sampling device, wherein an inner peripheral edge of said mask component defining said opening is beveled;
    placing said mask component on said target surface;
    wiping said prescribed area of said target surface with said sampling device, wherein said step of wiping comprises wiping an area delineated by said opening in said mask component; and
    examining said sampling device to determining a cleanliness of the target surface.

11. A method as in claim 10, wherein said examining step comprises measuring a reflectivity of a surface of said sampling device.

12. A method as in claim 10, wherein said sampling device includes a main body having an operative surface, and a debris collecting component removably disposed on said operative surface, said operative surface of said sampling device being convexly curved and further comprising removing said debris collecting component from said main body before said examining step.

13. A method as in claim 12, wherein said opening defines a surface area greater than a surface area of said operative surface of said sampling device.

14. A method as in claim 10, wherein said step of wiping is repeated at least once with a same surface of said sampling device, before said examining step.

* * * * *